(12) United States Patent
Meiners et al.

(10) Patent No.: US 8,571,841 B2
(45) Date of Patent: *Oct. 29, 2013

(54) SYSTEM AND METHOD OF SUB-SURFACE SYSTEM DESIGN AND INSTALLATION

(76) Inventors: Robert E. Meiners, Anchor, IL (US); Chad R. Meiners, Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/442,205

(22) Filed: Apr. 9, 2012

(65) Prior Publication Data

US 2013/0013266 A1    Jan. 10, 2013

Related U.S. Application Data

(63) Continuation of application No. 12/889,831, filed on Sep. 24, 2010, now Pat. No. 8,155,935, which is a continuation of application No. 11/939,089, filed on Nov. 13, 2007, now abandoned, which is a continuation of application No. 10/614,221, filed on Jul. 8, 2003, now Pat. No. 7,315,800.

(51) Int. Cl.
*G06F 17/50*    (2006.01)

(52) U.S. Cl.
USPC .................................. 703/7; 172/4.5; 37/348

(58) Field of Classification Search
USPC ................................ 703/2, 7; 172/4.5; 37/348
See application file for complete search history.

(56) References Cited

U.S. PATENT DOCUMENTS

| | | | | |
|---|---|---|---|---|
| 4,244,123 A * | 1/1981 | Lazure et al. | | 37/348 |
| 4,677,555 A * | 6/1987 | Goyet | | 701/50 |
| 5,519,620 A * | 5/1996 | Talbot et al. | | 701/2 |
| 5,602,741 A * | 2/1997 | Talbot et al. | | 701/470 |
| 5,757,646 A * | 5/1998 | Talbot et al. | | 701/2 |
| 5,995,895 A | 11/1999 | Watt et al. | | |
| 6,070,673 A * | 6/2000 | Wendte | | 172/2 |
| 6,236,907 B1 * | 5/2001 | Hauwiller et al. | | 700/283 |
| 7,315,800 B2 * | 1/2008 | Meiners et al. | | 703/7 |
| 8,155,935 B2 * | 4/2012 | Meiners et al. | | 703/2 |
| 2002/0162668 A1 * | 11/2002 | Carlson et al. | | 172/4.5 |
| 2004/0168358 A1 * | 9/2004 | Stump | | 37/348 |

* cited by examiner

*Primary Examiner* — Thai Phan
(74) *Attorney, Agent, or Firm* — 24IP Law Group; Timothy R. DeWitt

(57) ABSTRACT

The system and method of the present invention provides comprehensive design and installation management for agricultural water management systems. Maps and grade profiles are created from data collected by Global Positioning devices in the field. Latitude, longitude, and elevation are triangulated from GPS data to develop contour, grade, and profile maps, used to design drainage systems in real time. Customer billing information and vendor pricing information are produced from map and grade profile data. Interfacing and machine control for machines used to install drainage and/or irrigation systems are generated from contour, grade and profile data. Data is exported and imported in common file formats for efficient data exchange.

8 Claims, 4 Drawing Sheets

SYSTEM AND METHOD OF SUB-SURFACE SYSTEM DESIGN AND INSTALLATION

CROSS-REFERENCE TO RELATED APPLICATIONS

The present application is a continuation of and claims the benefit of the filing of U.S. Non-provisional patent application Ser. No. 12/889,831, which was filed by the present inventors on Sep. 24, 2010 now U.S. Pat. No. 8,155,935, which is a continuation of U.S. Non-provisional patent application Ser. No. 11/939,089, which was filed by the present inventors on Nov. 13, 2007 now abandoned and which is a continuation of and claims the benefit of U.S. Non-provisional patent application Ser. No. 10/614,221, now U.S. Pat. No. 7,315,800, which was filed by the present inventors on Jul. 8, 2003.

STATEMENT REGARDING FEDERALLY SPONSORED RESEARCH OR DEVELOPMENT

Not applicable.

BACKGROUND OF THE INVENTION

1. Field of the Invention

The present invention relates broadly to the field of agriculture, and more specifically to the use of topographic data in the field of agriculture.

2. Description of the Related Art

In the field of agriculture, irrigation systems water crop fields, and tile systems are manage water drainage in crop fields. Often, irrigation and tile systems are "sub surface," or installed under ground. Networks of pipe and/or tubing are installed underground for both systems, including main collector lines and a number of outlets. Outlets drain excess water into non-crop areas or drainage ditches which move the water away from crop fields. One or more junction boxes may be installed to check flows, sub mains, and drains. Irrigation and tiling systems are placed to provide the surrounding topography the best possible water supply and drainage. Additionally, outlets are placed where they are best protected from erosion, settlement, rodents, silting, shifting and damage by machinery and livestock. Discharge outlets further must be placed above the natural water level or bottom of a drainage ditch so that discharged water can drain freely.
Generally, this requires drainage to be staged at various grades, effectively using gravity to effect draining. However, where needed, pumps can be installed to facilitate drainage.

In order to properly position and install sub surface systems, contractors must assess the topography of the land. To do so, a topographical map of the area is prepared. A topographical map represents a three-dimensional land surface on a two-dimensional plane, for example, a map on a piece of paper. A topographical map uses lines and symbols to represent features in relation to the earth's surface. Terrain shape and elevation are depicted with contour lines.

To prepare a topographical map, a survey must be taken to determine horizontal and vertical measurements of various elevation points. These horizontal and vertical measurements can be gathered either by using a Global Positioning Systems (GPS) or surveying from a known benchmark. Specific elevation points are triangulated, and topographical maps are developed by hand from the triangulated data set.

Using the topographical map, an engineer and/or contractor, typically, uses the information to design a tile system. The topographical map further provides elevational information that is especially important to programming machine tools used to install the tile system.

Other current systems collect data points using survey grade, Real-Time Kinematic (RTK) Differential Global Positioning Systems (DGPS). In order to generate a topographical map from the RTK system data, the collected data must first be transferred to a CAD program. The latitude, longitude, and altitude coordinates must be converted into a datum set for compatibility with CAD. The profile is then developed in CAD. Automated installation machines are grade controlled using the topographic map, and use the latitude, longitude, and altitude data generated by the RTK system. To use the topography data generated by CAD, the x,y,z datum sets must be converted back to latitude, longitude, and altitude data points. This repeated conversion degrades the precision of the data point locations. Further, current systems use the highly expensive RTK equipment with the installation machines to try and correct for the error, thus adding significant cost.

Another problem associated with using RTK GPS systems to create topographical maps is dependency on benchmark and base station locations which can shift over time. A benchmark is a reference object. Topographic coordinates are measured from the base station or benchmark location. The setup of a base station is inconvenient, time consuming, and introduces error into the survey if the exact position cannot be located again. The position of benchmark objects, such as trees, buildings, and stones, may be shifted or eliminated all together over time. Thus, locating the base station and benchmarks becomes a serious problem for future use.

Another problem arises from the type of survey equipment required with current systems. Many known systems require data points to be collected using laser survey equipment to compensate for the accuracy loss caused by multiple data conversions. Laser equipment is very costly, increasing both the contractor and farmer's expense.

Yet another problem with present systems and methods is that maps cannot be created in the field either in real time or from a single program. Instead, current systems address only one function at a time, and do not integrate and stream line the design and build process.

Still another problem with current systems stems from relying on footage measurements. After maps are created, the objects of the map cannot be easily located by latitude, longitude, and altitude using global positioning devices. Points have to be converted to footage from a known benchmark. The benchmarks are not easily located years after the map is created. Since the combination of different computer programs is required, the cost and time is substantial. Organization of computer data files for one project is difficult and requires the storing of many files. The probability of using the data in future projects is difficult.

Tile machines are used to dig out and fill in subsurface areas where tiling components are placed in a field. Currently, to exercise grade control over machines, each one must have an expensive RTK system. Further, using known systems and methods of drainage system design management, an RTK system would be needed for the initial survey and for each tiling machine. Since RTK systems are quite expensive, the system designer bears heavy costs for the necessary equipment.

Still another problem with current systems is that they do not provide data used for preparing estimates, billing, and generally providing business-related information. Thus, when using current systems, a contractor must purchase business related software and manually enter data associated with materials and labor for a proposed system design.

Although prior systems, methods, and devices generally functioned well and provided advantages over prior systems, methods, and devices, they do not provide users with an integrated system of tiling system design management. They further do not provide integrated mapping and tooling. They also do not provide a cost-effective means for designing various types of systems where topographic information is needed in the design process.

SUMMARY OF THE INVENTION

The present invention has been made in view of the above circumstances and has as an aspect to provide a system and method of managing the design and installation of agricultural water management systems. Another aspect of the present invention is to provide a comprehensive system and method of managing the design and installation of water management systems, which reduce the amount of interface equipment, and reduce cost.

The system and method of the present invention provides comprehensive design and installation management for water management systems. Maps and grade profiles are created from data collected by Global Positioning devices in the field. Latitude, longitude, and elevation are triangulated from GPS data to develop contour, grade, and profile maps, used to design irrigation and drainage systems in real time. Customer billing information and vendor pricing information are produced from map and grade profile data. Interfacing and machine control for machines used to install irrigation and/or drainage systems are generated from contour, grade and profile data. Data is exported and imported in common file formats for efficient data exchange.

Still other aspects, features, and advantages of the present invention are readily apparent from the following detailed description, simply by illustrating preferable embodiments and implementations. The present invention is also capable of other and different embodiments, and its several details can be modified in various respects, all without departing from the spirit and scope of the present invention. Accordingly, the drawings and descriptions are to be regarded as illustration in nature, and not as restrictive.

BRIEF DESCRIPTION OF THE DRAWINGS

The accompanying drawings, which are incorporated in and constitute a part of this specification illustrate some embodiments of the invention and, together with the description, serve to explain the objects, advantages, and principles of the invention. In the drawings.

DETAILED DESCRIPTION OF THE PREFERRED EMBODIMENTS

Figure 1:
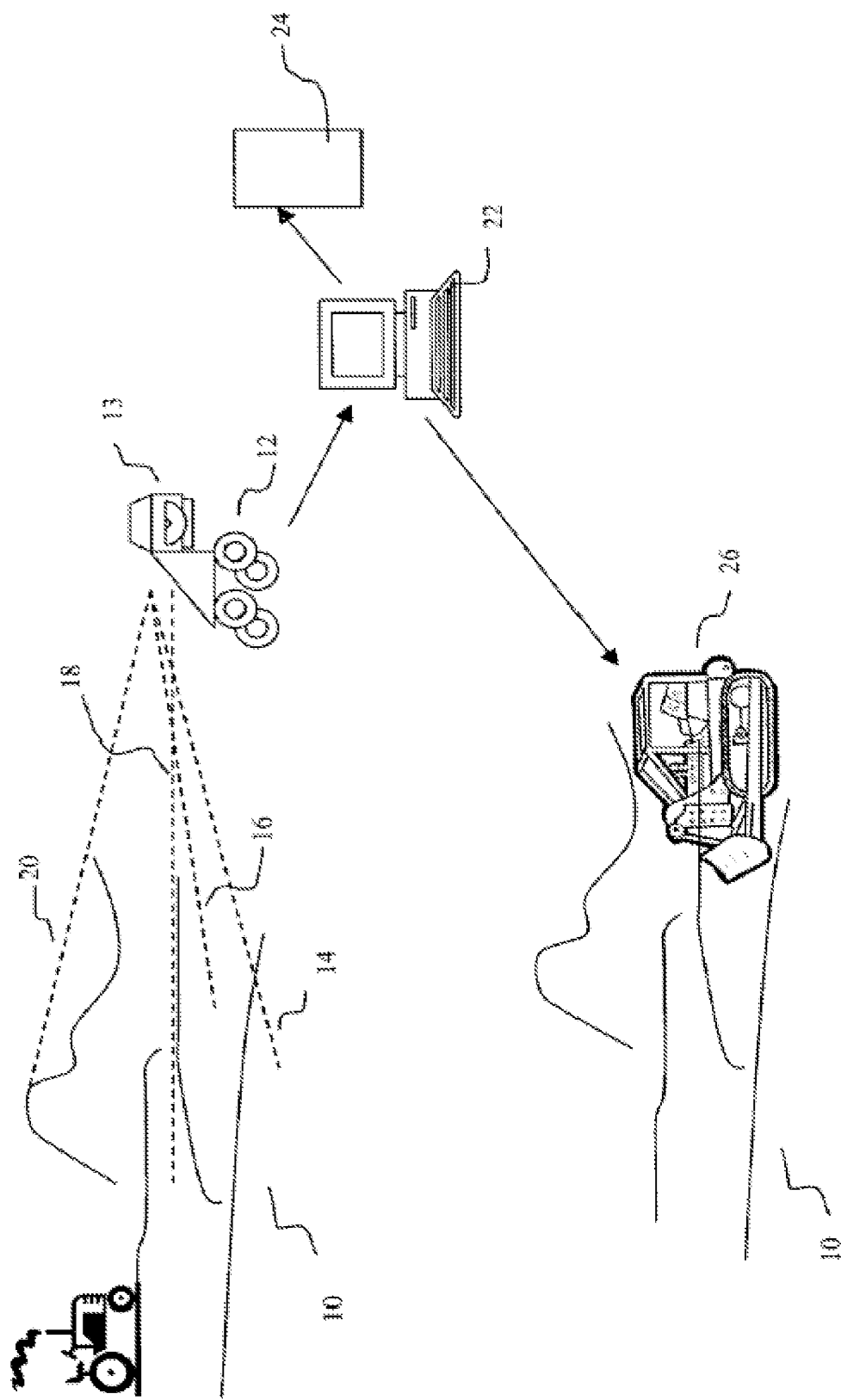
FIG. 1 is a preferred embodiment of a management system in accordance with the present invention.

FIG. 1 illustrates a preferred embodiment of the present invention. An agricultural field 10 requires a drainage system. A mobile vehicle 12 carries an RTK system including a computer having an Input/Output (I/O means) 13 for uploading and downloading data to the RTK system. Preferably the RTK system includes a rugged computer encased to protect the computer from the elements and shock from traveling over the rough terrain. The mobile vehicle may take a variety of forms, such as ATV'S, construction equipment, tractors, trucks, cars, boats, ships, helicopters, airplanes, or the like. A computer having at least a 2.0 Gigahertz processor, a 20 Gigabyte hard drive, and 128 Megabytes of volatile memory is preferred for use with the present invention, although computer having different or less capability may be used as well. The rugged computer stores and executes software for surveying an area using GPS coordinates. The RTK system is used to survey and gather very accurate data points for creating a contour map of the area specified.

The mobile vehicle 12 travels around a perimeter of the field 10 with the mapping program automatically records the latitude and longitude coordinates of the vehicle from the RTK device at predetermined intervals, for example, every five feet. Next, the system is used to map the area in the field 10. Data points are gathered in sections. For example, a given field may preferably be divided into 25-foot swaths. In each section, coordinates of a high point 18, a low point 14, as well as depressions 16 or high points 20 that may not be in a particular swath are gathered. Each point has a latitude, longitude and altitude coordinate.

Once the survey data is gathered, survey data is transferred through the 110 means 13 to a management station 22. Preferably, a flash card inserted into the 110 means 13 is used to download survey data from the RTK system. However, it will be appreciated by one skilled in the art that a variety of mediums, for example, CD ROMs and diskettes, may be used. Additionally, it will be appreciated by one skilled in the art that wireless embodiments may be used without departing from the scope of the present invention. Once the data is transferred to the management station 22, it may be used to generate a contour map of the field 10, which is further used to design irrigation and drainage systems, and calculate costs to install these systems.

Figure 2:
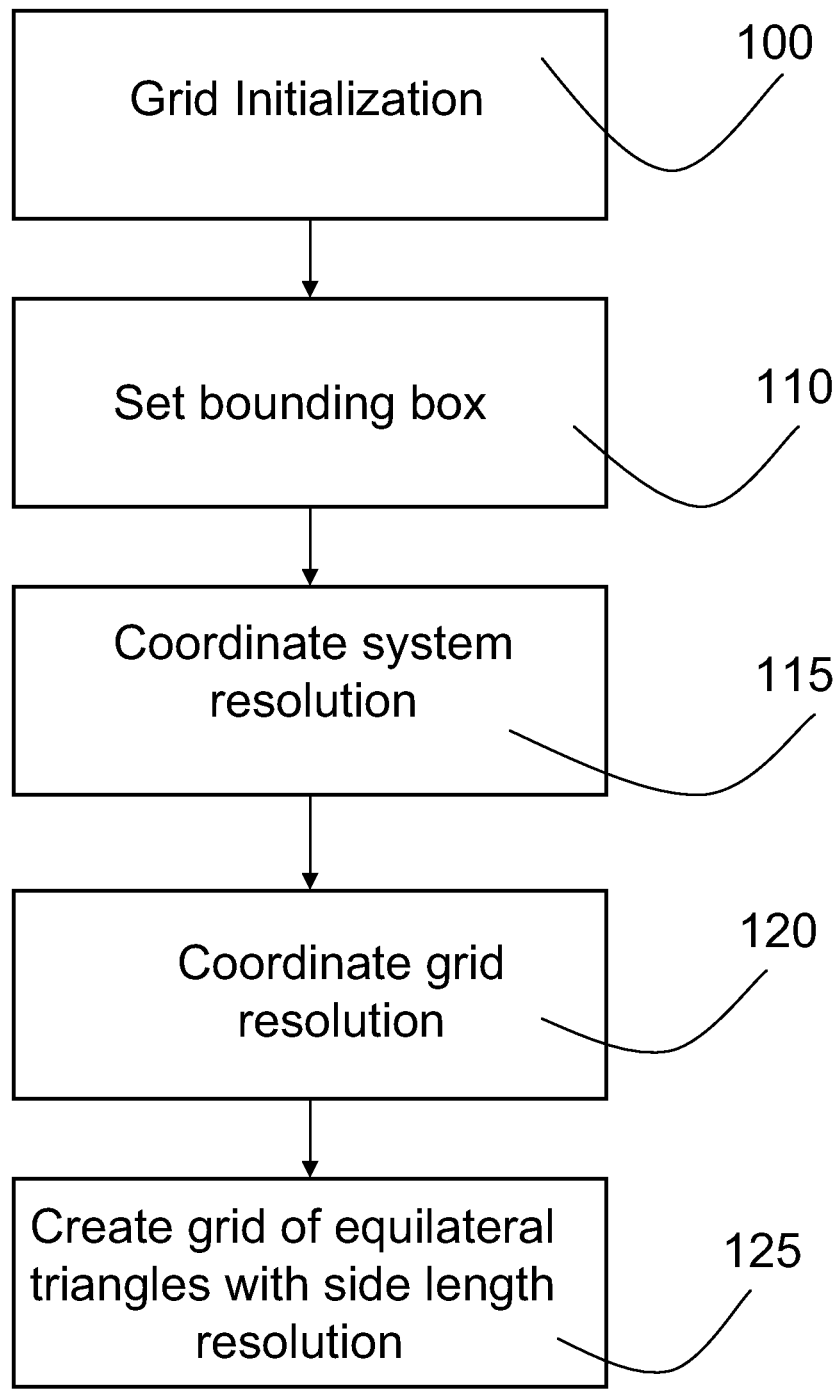
FIG. 2 is a logic flow diagram of a portion of the mapping process in accordance with the present invention, namely, grid initialization.
Figure 3:
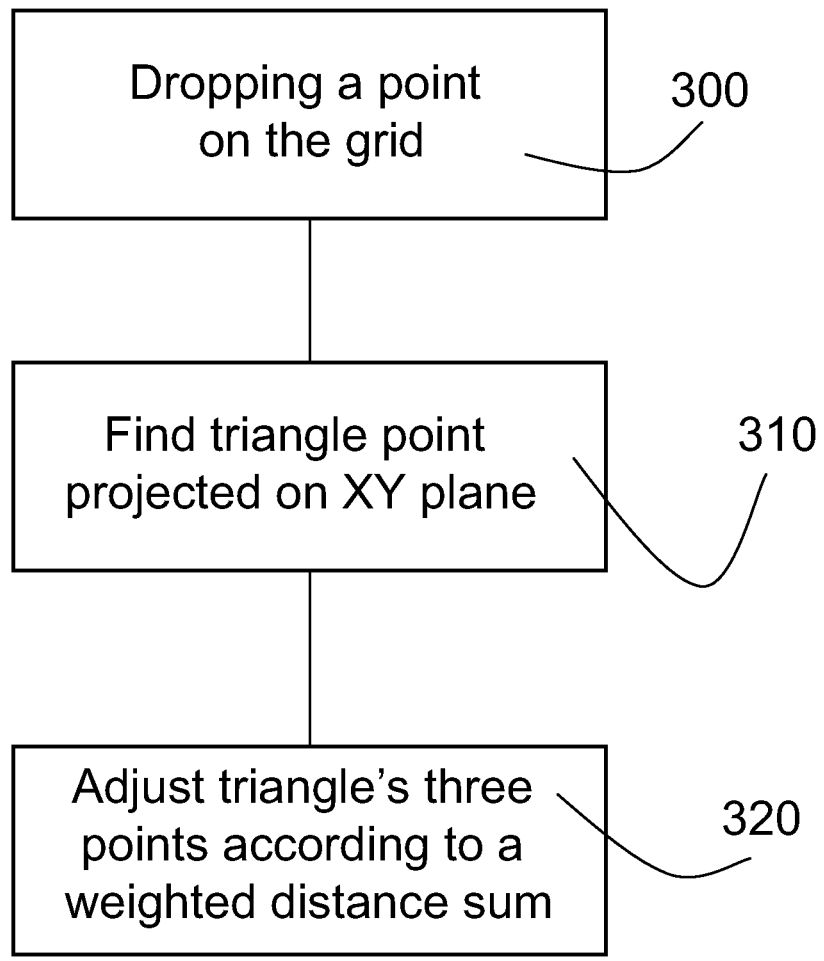
FIG. 3 is a logic flow diagram of a portion of the mapping process in accordance with the present invention, namely, querying the altitude of a point.
Figure 4:
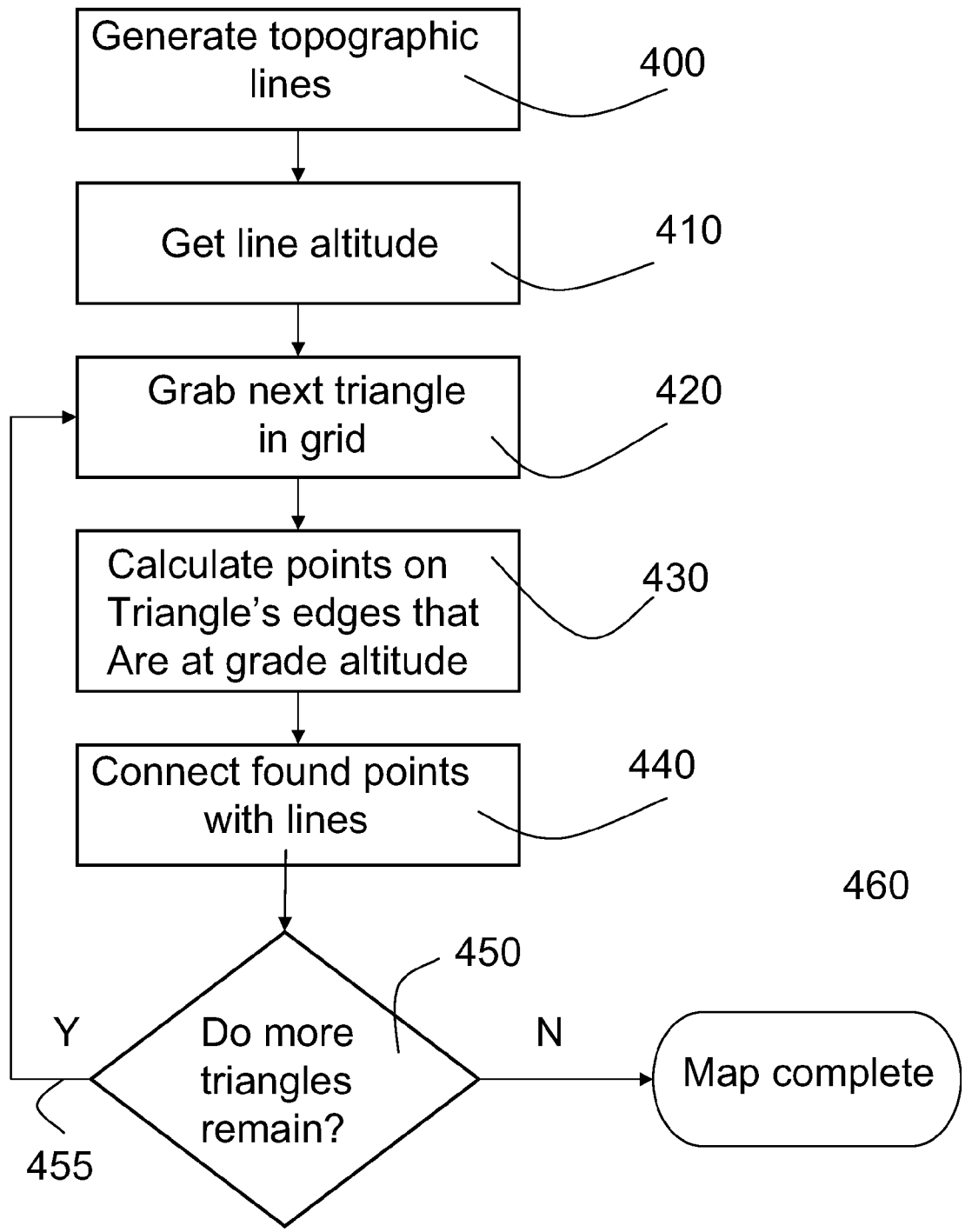
FIG. 4 is a logic flow diagram of a portion of the mapping process in accordance with the present invention, namely, generating topographical lines.

The management station 22 is preferably a personal computer having a processor and memory. The management station 22 stores and executes a computer program for generating contour maps, designing irrigation and drainage systems, estimating costs to install irrigation and drainage systems. Referring to FIGS. 2-4, creating a contour map in accordance with the present invention is illustrated. The mapping process includes 3 parts: grid initialization 100, querying the altitude of a point 300, and generating topographic lines 400. For grid initialization 100, a bounding box is identified 105 according to the longitude, latitude and altitude of each point on the perimeter. Next, the coordinate system resolution 115 is performed by identifying the longitude, latitude and altitude of each data point (14, 16, 18, 20) identified in the field 10. It will be appreciated by one of ordinary skill in the art that selecting more data points in the initial survey, i.e., having a finer grid resolution, will result in smoother contour lines. Create a grid of equilateral triangles with side length resolution 125.

Referring to FIG. 3, the process of querying the altitude of a point of the mapping process of the present invention is illustrated. Querying the altitude of a point on the grid comprises the steps of dropping point on the grid, finding a triangle point projected on the XY plane 210, and adjusting the triangle's three points according to a weighted distance sum.

Referring to FIG. 4, the process of generating topographical lines of the mapping process of the present invention is illustrated. Generate topographic lines 400. Get line altitude 410. Grab next triangle in grid 420. Calculate points on triangle's edges that are at grade altitude 430. Connect found points with lines 440. Next, the counter looks for whether any more triangles remain 450. If triangles do remain 455, the process continues back to step 420 to grab the next triangle. If no triangles remain, the grid overlay is complete 460. The topographical map shows points at equal elevations connected to each other.

Referring again to FIG. 1, the finished contour map and related date is then used to carry out other functions related to designing and installing irrigation and drainage systems. The management station 22 stores and executes software for designing these systems, as well as managing a variety of business calculations related to the cost of installing a proposed system. The design of the tile system is created by drawing tile lines over the contour map, and calculating the elevation from the mapping triangulation, described above. The design program provides data for the tile location, grade, flow, and size. Also using the contour map data, the location, grade, size and acreage of each terrace in the design is calculated. Location, grade, flow, and size of cleared surfaces is also calculated. The program uses the tile size and footage of the designed system to calculate a cost estimate 24. The program can prepare a variety of estimates 24 including costs from more than one vendor. A copy of the contour map and proposed irrigation or drainage system generated 24 may also be given to the customer.

Irrigation or drainage design data is transferred via a transfer means (not shown), such as a flash card, from the management station 22 to at least one machine tool 26 used to dig and install the tiling system. Typically, the machine tool 26 is a tile plow. However, it will be appreciated that a wide variety of construction machines may be used without departing from the scope of the present invention. The machine tool 26 is controlled by instructions generated by the management station 22. If the machine tool 26 includes a grade control mechanism, such as a laser, a combined laser and DGPS, or RTK system, then the contour map may be used without further calculation. However, when the machine tool 26 does not include such grade controls, objects are flagged to indicate digging locations. The machine tool 26 then digs and installs tiles or irrigation devices according to the locations on the map. If the machine tool 26 includes an interface for machine control, the machine tool 26 will only need a laser system with sub meter DGPS. The RTK system on the mobile vehicle may be used at this time to gather more data points for new projects or compliment data gathered by the tile machine. However, it is not required. Thus, from survey through installation, only one RTK system is required for the entire operation.

The machine tool 26 maps where each tile is actually placed while installing the tile. A final map and bill is produced for the customer. With the final map, either the contractor or customer can locate tiles from the DGPS coordinates, and does not need a benchmark.

In an alternative embodiment, machine controls for multiple grades use the map printout and grade profiles for standard $1/10$ grade with just laser control. For problem areas with multiple grades, a multi-grade profile printout can be used for reference by a person who controls the grade of the machine manually. Manual control is accomplished by measuring the footage the machine tool 26 travels and then changing the grade at pre-determined footage break points. Using the manual-control embodiment, the GPS model used in conjunction with the machine tool 26 can have a lesser degree of accuracy, saving the customer from additional costs. Thus, the present invention allows for controlling the machine tool 26 using global positioning devices that have different degrees of accuracy. Specifically, devices having no differential correction with accuracy between 9-15 feet, devices with differential correction and accuracy within 9 feet, devices with differential correction and sub-meter accuracy, and differential correction and an accuracy within 3 centimeters.

If desired, the RTK mobile vehicle could then be used to map where the tile lines and other features of the system are located during the installation process.

It will be appreciated by one skilled in the art that, while the present system and method is described in the context of drainage systems and irrigation systems installed below ground level, the present invention may be used in a variety of contexts where contour and grade information is needed. Examples of such systems include spin ditches and waterways. Further, such systems may be used to install non-agricultural systems, for example, fiber-optic networks or sewage systems, which require below-ground components.

Though the preferred embodiment is described as collecting data points which are transferred to the management station 22, it will be appreciated by one skilled in the art that the data points may be processed at the computer of the mobile vehicle 12 without departing from the scope of the present invention.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What we claim is:

1. A system for designing sub surface systems in an area comprising:
    a Global Positioning System;
    a first computer comprising a processor and a storage means, wherein said first computer is connected to said Global Positioning System and said first computer collects and stores data of said area;
    a second computer, wherein said second computer receives data of said area collected and stored by said first computer, analyzes said received data, prepares a contour map of said area from said received data and designs a drainage system for said area.

2. A system for designing sub surface systems in an area according to claim 1, further comprising:
    means for generating an instruction set based on said received data to control machinery during installation of said drainage system for said area.

3. A system for designing sub surface systems in an area according to claim 1, further comprising:
    a controller for controlling a machine tool to install said drainage system.

4. A method for designing a drainage system comprising the steps of:
    gathering GPS data of a field, said GPS data comprising a longitude, latitude and altitude of a plurality of points along a perimeter of said field and an interior of said field;
    generating a contour map of said field using said gathered GPS data; and designing a drainage system from said contour map and said GPS data.

5. A method for designing a drainage system according to claim 4, further comprising the step of displaying said contour map.

6. A method for designing a drainage system according to claim 4, further comprising the step of generating control data for controlling a machine to install said drainage system.

7. A system for designing a drainage system in an area comprising:
- a Global Positioning System; and
- a computer, said computer comprising:
    - an input for receiving position data of said area from said Global Positioning System;
    - a storage means for storing received position data of said area; and
    - a processor;
    - wherein said processor analyzes received position data, generates a contour map of said area from said received position data and generates a design for a drainage system for said area.

8. A system for designing a drainage system in an area according to claim 7, wherein said processor generates control data for controlling a machine to install a designed draining system based on said contour map for said area.

* * * * *